United States Patent
Blank et al.

(10) Patent No.: US 10,718,840 B2
(45) Date of Patent: Jul. 21, 2020

(54) METHOD FOR PREPARATION OF HIGHLY POLARIZED NUCLEAR SPINS CONTAINING SAMPLES AND USES THEREOF FOR NMR AND MRI

(71) Applicants: TECHNION RESEARCH & DEVELOPMENT FOUNDATION LIMITED, Haifa (IL); YEDA RESEARCH AND DEVELOPMENT CO. LTD., Rehovot (IL)

(72) Inventors: Aharon Blank, Kefar Veradim (IL); Itai Katz, Nofit (IL); Akiva Feintuch, Lod (IL)

(73) Assignees: Technion Research & Development Foundation Limited, Haifa (IL); Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 15/738,688

(22) PCT Filed: Jun. 26, 2016

(86) PCT No.: PCT/IL2016/050691
§ 371 (c)(1),
(2) Date: Dec. 21, 2017

(87) PCT Pub. No.: WO2017/002113
PCT Pub. Date: Jan. 5, 2017

(65) Prior Publication Data
US 2018/0180696 A1  Jun. 28, 2018

Related U.S. Application Data

(60) Provisional application No. 62/186,405, filed on Jun. 30, 2015.

(51) Int. Cl.
| | | |
|---|---|---|
| *G01R 33/56* | (2006.01) | |
| *G01R 33/30* | (2006.01) | |
| *G01R 33/62* | (2006.01) | |
| *A61K 49/20* | (2006.01) | |
| *G01R 33/28* | (2006.01) | |
| *A61B 5/055* | (2006.01) | |
| *A61M 5/00* | (2006.01) | |
| *G01R 33/48* | (2006.01) | |

(52) U.S. Cl.
CPC .......... *G01R 33/5601* (2013.01); *A61B 5/055* (2013.01); *A61K 49/20* (2013.01); *A61M 5/007* (2013.01); *G01R 33/282* (2013.01); *G01R 33/62* (2013.01); *A61M 2005/006* (2013.01); *G01R 33/4806* (2013.01)

(58) Field of Classification Search
CPC .......... G01R 33/30; G01R 33/56; G01R 33/62
See application file for complete search history.

(56) References Cited

U.S. PATENT DOCUMENTS

| | | | | |
|---|---|---|---|---|
| 5,306,505 | A * | 4/1994 | Kuzuya | A61K 9/2853 424/464 |
| 2004/0039281 | A1 | 2/2004 | Cook et al. | |
| 2016/0033590 | A1* | 2/2016 | Eichhorn | G01R 33/282 324/318 |

FOREIGN PATENT DOCUMENTS

| | | |
|---|---|---|
| JP | 61140846 A | 6/1986 |
| WO | 2014139573 A1 | 9/2014 |

OTHER PUBLICATIONS

J. Heckmann et al. Electron spin resonance and its implication on the maximum nuclear polarization of deuterated solid target materials, Physical Review B 74, 134418. (Year: 2006).*
Levêque P.P. et al., "Spin density distribution in foodstuff after heat treatment or irradiation", Proceedings of the International Society for Magnetic Resonance in Medicine, 16th Scientific Meeting and Exhibition, Toronto, Canada, p. 1733. (2008).
C.H. Bamford et al, "The effect of the high-frequency discharge on the surfaces of solids. I-The production of surface radicals on polymers", Polymer., GB, vol. 2 pp. 277-293.(1961).
Extended European Search Report (EESR) dated Feb. 14, 2019.
Sasai, Y. et al; "Cold Plasma Techniques for Pharmaceutical and Biomedical Engineering" Biomedical Engineering, Trends in Materials Science. pp. 101-122. (2011).
Katz, I. et al; "Dynamic nuclear polarization in solid samples by electrical-discharge-induced radicals" Journal of Magnetic Resonance 261 pp. 95-100. (2015).
International Search Report and Written Opinion dated Oct. 9, 2016, from International Application No. PCT/IL2016/050691, 11 pages.

* cited by examiner

*Primary Examiner* — Michael G. Hartley
*Assistant Examiner* — Jagadishwar R Samala
(74) *Attorney, Agent, or Firm* — Meunier Carlin & Curfman LLC (57) ABSTRACT

A method for the preparation of a highly polarized nuclear spins containing sample of an organic or inorganic material, containing H or OH groups or adsorbed water molecules. Such highly polarized nuclear spins containing samples can be subjected to nuclear magnetic resonance (NMR) measurement and/or can be thawed and immediately administered to an individual undergoing a magnetic resonance imaging (MRI) scan. The method is based on generating unstable radicals on the surface of the sample in the presence of ionized environment followed by cooling the sample to cryogenic temperatures. A device for carrying out a particular step of said method is also discloses.

7 Claims, 9 Drawing Sheets

METHOD FOR PREPARATION OF HIGHLY POLARIZED NUCLEAR SPINS CONTAINING SAMPLES AND USES THEREOF FOR NMR AND MRI

CROSS-REFERENCE TO RELATED APPLICATIONS

This application is a U.S. National stage application of International Application No. PCT/IL2016/050691, filed Jun. 26, 2016, designating the U.S. and published as WO 2017/002113 on Jan. 5, 2017, which claims priority to and the benefit of U.S. Provisional Application No. 62/186,405, filed Jun. 30, 2015. These above-identified applications are hereby incorporated by reference in their entireties.

TECHNICAL FIELD

The present invention relates to a method for the preparation of highly polarized nuclear spins containing samples, and uses thereof.

Abbreviations: DFT, density functional theory; DNP, dynamic nuclear polarization; EDIR, electrical discharge induced radical; ESR, electron spin resonance; MRI, magnetic resonance imaging; NMR, nuclear magnetic resonance; RF, radio frequency; SNR, signal to noise ratio.

BACKGROUND ART

NMR is a field of science with applications ranging from basic physics and chemical analysis to medical imaging and diagnostics (MRI). NMR relies on picking up RF signals from nuclear spins transiting between energy levels created as an external magnetic field is applied. The spectral properties of the NMR signal are highly influenced by the microscopic environment of the observed nuclei hence providing detailed information on that environment. This gives NMR its informative power, unparalleled by any other spectroscopic technique.

Despite this, NMR suffers from an inherently low SNR which poses severe limitations on its applicability. An NMR sample must be relatively large and materials found in it in trace amounts cannot be detected, despite the great importance they might have. Such is the case, e.g., in the investigation of surfaces, a thriving scientific field in its own right. The actual amount of material found at the surface is a very small percentage of most samples. But virtually all dynamical processes, such as catalysis or corrosion, occur at the surface. So, to access the surface with NMR spectroscopy is an important scientific goal that cannot be achieved with regular magnetic resonance. The SNR problem is also encountered in the MRI field, where the low sensitivity limits the scope of the measurement only to the bulk constituents of the human body, i.e., water and fat. All the interesting parts, such as proteins, hormones, genetic material, etc., are usually completely transparent, unless extremely specialized and unique protocols are employed. The sensitivity problem is also the bottle neck factor limiting image resolution.

The low SNR also mandates that multiple identical measurements be averaged out in order to reach a reasonable prominence of the data. This renders NMR measurements very lengthy in time, and their length usually grows exceedingly with the complexity of the examined system. Some "holy grail" applications such as metabolic MRI or advanced quantum computing are not even attempted due to ridiculously long experiment durations. Implementation of sophisticated measurement protocols, two-dimensional NMR for instance, is hindered substantially by the lengthiness problem. In MRI, this problem is manifested in very lengthy examinations, which are uncomfortable for the patients and reduce the availability of MRI examinations. It also comes into play when one wishes to take rapid scans in order to image body parts as they move (e.g., heart MRI).

The above examples illustrate that the SNR-sensitivity problem is of central importance in the NMR field whether in its scientific research branch or in its medical branch. The circumvention of this acute problem is thus of great importance and several techniques aimed at it are present. Those techniques are often referred to as hyperpolarization techniques and include, e.g., para-hydrogen, pre-polarization, optical pumping, and DNP.

DNP is a technique that enables the transfer of magnetization from a highly polarized population of unpaired electron spins, known as polarizing agents, onto the much more weakly polarized population of nuclear spins (Maly et al., 2008; Abragam and Goldman, 1978). Since its first demonstration as a manifestation of the Overhauser effect in low fields (Carver and Slichter, 1956), DNP has attracted much interest both as means to dramatically increase the faint NMR signal (Ardenkjær-Larsen et al., 2003) and as a scientifically interesting phenomenon in its own right (Hu et al., 2011). Consequently, DNP has found recent applications ranging from structural biology (Barnes et al., 2008) and NMR of surfaces to experimental metabolic MRI used for clinical diagnosis (Nelson et al., 2013; Mishkovsky et al., 2012; Golman et al., 2006). The magnetization enhancement factor for protons obtainable by DNP, which is calculated as the ratio between the hyper-polarized and the normal thermal (Boltzmann) magnetizations, has a theoretical maximal value of ~658. In practice, however, enhancement factors are usually several times smaller than the maximal theoretical ones (typically 10-100). An increase in magnetization by a given factor speeds up the NMR experiment quadratically, and in this respect the hyper polarization obtained by DNP is of great value.

The common method of obtaining efficient DNP enhancements in molecules of interest is to dissolve them in the presence of unique stable free radicals (polarizing agents) (Maly et al., 2008; Song et al., 2006) and then cool the solution to low cryogenic temperatures, where an appropriate microwave irradiation resonant with free radicals can transfer the spin polarization from the electrons to the nuclei of interest (Maly et al., 2008; Abragam and Goldman, 1978). Following this, the sample can be measured as is, using solid state NMR (Barnes et al., 2008), or undergo rapid dissolution to be measured in the liquid state (Ardenkjær-Larsen et al., 2003), while preserving most of its spin polarization. This fairly established procedure is very effective, but yet possesses some challenges: The most trivial hindrance stems from the polarizing agents' chemical uniqueness and cost, which can amount to hundreds of dollars per milligram for some species. A more profound problem that plagues the use of DNP is the necessity to achieve molecular-level mixing between sample molecules and polarizing agents, obtainable only in a solvent environment. Given that this is not always the native environment of the sample, much care and experimental optimization must be exercised in order to arrive at a successful DNP experiment whilst preserving the sample's key features (Lesage et al., 2010). Furthermore, a highly serious problem concerns the use of DNP for medical purposes, due to the incompatibility of existing stable radicals with the human body, and thus severely limits the introduction of the DNP technique into the clinic (Dollmann et al., 2010). While several solutions to this problem exist in various stages of maturity (Dollmann et al., 2010; Eichhorn et al., 2013; Ardenkjaer-Larsen et al., 2011), they are far from being comprehensive.

In light of the above, it might be highly beneficial to supplement the current arsenal of polarizing agents with additional, preferably endogenic, types that are complementary to the existing ones, and without going through the solution phase.

International Publication No. WO 2014139573 discloses a method for the preparation of highly polarized nuclear spins containing sample, aimed at enhancing the SNR in NMR and MRI measurements thus shortening these measurements. The concept underlying the method disclosed is the generation of radicals in the solid state, which are then used in a DNP process prior to the NMR measurement or MRI scan. This method necessitates the presence of carbonyl groups on the material treated, more particularly, the alpha- and/or gamma-diketone functional groups $R_1$—C(O)—C(O)—$R_2$ and $R_1$—C(O)—C=C—C(O)—$R_2$, respectively, and uses electromagnetic irradiation in the visible or UV range so as to generate radicals from those carbonyl groups. According to this publication, the irradiation process takes about an hour or more.

Another method of relevance achieves DNP of solid samples without dissolving them in solution by impregnating powdered sub-micron sized samples with non-solvents (Rossini et al., 2014). However, the impregnation steps and sample grinding can cause phase transitions between polymorphs in some cases (Pinon et al., 2015).

SUMMARY OF INVENTION

In one aspect, the present invention thus relates to a method for the preparation of a sample comprising highly polarized nuclear spins, said method comprising:
  (i) providing a sample, in the form of a powdery solid, in a sealed vessel;
  (ii) generating unstable radicals in said sample by electrical ionization of the gas environment in said vessel, or by subjecting said sample to ionizing radiation with an energy not less than 25 eV; mechanical agitation; or heat treatment, wherein said unstable radicals are fixed to the solid and thus do not decay;
  (iii) cooling said sample to a cryogenic temperature; and
  (iv) performing dynamic nuclear polarization (DNP) process on the cooled sample so as to transfer spin polarization from the electron spins to the nuclear spins, thereby obtaining said sample comprising highly polarized nuclear spins.

Preferably, the method of the present invention further comprises the step of setting a controlled pressure and composition gas environment in said vessel, prior to, during, or immediately after, step (ii). In particular such embodiments, the step of setting a controlled pressure and composition gas environment in said vessel is carried out prior to, and optionally during, step (ii), e.g., by evacuating gas from said vessel leaving a reduced pressure in said vessel.

The highly polarized nuclear spins containing sample obtained by the method of the present invention may be subjected to an NMR measurement; or thawed and then be subjected to an NMR measurement, or administered to a subject undergoing an MRI scan.

In certain embodiments, the method of the invention thus further comprises the step of subjecting the sample obtained in step (v) to an NMR measurement, e.g., a solid state NMR, magic-angle spinning (MAS)-NMR, or an NMR measurement for the investigation of a surface.

In other embodiments, the sample provided in step (i) of the method of the invention is an MRI contrast agent or a compound participating in a metabolic pathway occurring in the body of a subject undergoing an MRI scan, and said method further comprises the step of thawing the sample obtained in (v) and immediately administering said sample, in liquid or gaseous form, to said subject.

In another aspect, the present invention provides a sample comprising highly polarized nuclear spins obtained by the method as defined above in steps (i) to (v).

In a further aspect, the present invention provides a device, more particularly a radical generator, for carrying out step (ii) of said method, i.e., for generating unstable radicals in a powdery sample provided in a sealed sample tube, said device comprising:
  (i) a sample tube having (a) at least one opening comprising a valve, for optionally introducing a powdery sample and/or a solvent therein, and for evacuating gas from said sample tube and/or introducing a desired gas or gas composition therein; (b) optionally an additional opening capable of being hermetically sealed for inserting a powdery sample; and (c) optionally two internal electric contacts for connecting to an external electric power source and carrying electric power to cause electrical breaching of the atmosphere within said sample tube;
  (ii) optionally an inductor surrounding said sample tube, for connecting to a high frequency alternating current (AC) electric power source and carrying electric power to induce a strong circular electric field within said sample tube to thereby sustain an electric arc within said sample tube;
  (iii) an atmosphere control unit for connecting to said at least one opening of said sample tube, for evacuating gas from said sample tube and/or introducing a desired gas or gas composition into said sample tube; and
  (iv) optionally an electric power source for connecting and providing electric power to either said two internal electric contacts or said inductor,
  provided that either said two internal electric contacts or said inductor is present.

DETAILED DESCRIPTION

It has now been found, in accordance with the present invention, that free radicals generated in a solid sample of interest upon a short treatment in a dilute atmosphere ionized by electrical discharge, i.e., electrical discharge induced radicals, can serve as effective polarizing agents. Such plasma-induced radicals in solid powders have been known to exist for some time (Kuzuya et al., 1992) but have not been explored in the context of DNP.

Similar to the method disclosed in the aforesaid WO 2014139573, the method of the present invention is aimed at significantly enhancing the SNR in NMR and MRI measurements thus shortening these measurements by generating stable radicals in the solid state, wherein those radicals are then used in a DNP process, transferring spin polarization from electrons to nuclei, prior to the NMR measurement or MRI scan. However, the method of the present invention is substantially different from the one disclosed in WO 2014139573 in that the material treated by the former may be any organic or inorganic material containing H or OH groups or adsorbed water molecules, no matter whether carbonyl groups are present or not; and generation of radicals is carried out at a significantly shorter process, more particularly dozens of seconds vs. an hour, and using a technology other than UV irradiation, e.g., electrical ionization. Furthermore, in contrast to the method disclosed in WO 2014139573, the method of the present invention also works well with optically opaque solid materials with high surface area—generating radicals mainly on the surface of the sample.

In one aspect, the present invention relates to a method for the preparation of a sample comprising highly polarized nuclear spins, more particularly, a sample polarized in excess of Boltzmann polarization, said method comprising:
(i) providing a sample, in the form of a powdery solid, in a sealed vessel, e.g., tube;
(ii) generating unstable radicals in said sample by electrical ionization of the gas environment in said vessel, or by subjecting said sample to ionizing radiation with an energy not less than 25 eV; mechanical agitation; or heat treatment, wherein said unstable radicals are fixed to the solid and thus do not decay;
(iii) cooling said sample to a cryogenic temperature; and
(iv) performing dynamic nuclear polarization (DNP) process on the cooled sample so as to transfer spin polarization from the electrons of said unstable radicals to the nuclear spins, thereby obtaining said sample polarized in excess of Boltzmann polarization.

As stated above, the method of the present invention preferably further comprises the step of setting a controlled pressure and composition gas environment in said vessel, prior to step (ii), during step (ii), or immediately after step (ii) and prior to step (iii). In particular such embodiments, the step of setting a controlled pressure and composition gas environment in said vessel is carried out prior to, and optionally during, step (ii).

The term "sealed vessel" as used herein refers to a vessel such as a tube, e.g., NMR tube, having an inner environment that is isolated from its outer environment, i.e., the ambient atmosphere. In other words, the gas environment inside the vessel provided in step (i) of the method is isolated from the outer environment rather than permanently sealed, and the pressure and composition of said gas environment can thus be controlled, e.g., by evacuating gas from said vessel or by introducing a suitable gas into said vessel, prior to, during, or immediately after step (ii). In certain embodiments, the sealed vessel used is an ordinary (i.e., regular) tube such as a regular NMR tube, whereas in other embodiments said vessel may have an irregular shape, e.g., may be a bulged tube such as a bulged NMR tube, having a bulge in which the sample is placed in step (i). As shown herein, the bulge and consequently the increased volume of gas environment in said vessel may substantially increase the concentration of radicals generated (in step (ii)) in said sample as a result of, e.g., electrical ionization of the gas environment.

In certain embodiments, the method of the present invention further comprises the step of setting a controlled pressure and composition gas environment in said vessel, preferably prior to step (ii), wherein said step is carried out by evacuating gas from the sealed vessel, e.g., by a vacuum system, leaving a reduced pressure in the vessel. In particular such embodiments, the gas is evacuated from said vessel by a vacuum system maintaining a moderate vacuum level, e.g., of about $1 \times 10^{-6}$ to about $1 \times 10^{-3}$ bar, or about $0.5 \times 10^{-4}$ bar to about $2 \times 10^{-4}$ bar. It should be understood that the low pressure is necessary in order to preserve the radicals formed in step (ii). In other words, whereas radicals can theoretically be generated in step (ii), under certain conditions (e.g., strong voltage source), without first reducing the pressure in the vessel, such radicals would not be stable and could be preserved only if the pressure inside the vessel is immediately reduced, i.e., the atmosphere inside the vessel is diluted.

In other embodiments, the method of the present invention further comprises the step of setting a controlled pressure and composition gas environment in said vessel, preferably prior to step (ii), wherein said step is carried out by introducing a suitable gas into the sealed vessel, and creating a pressure that is lower than the initial pressure in said vessel. According to the present invention, the gas introduced into the vessel so as to set a controlled composition in said vessel may be any suitable gas, e.g., a noble gas such as helium, argon, neon, krypton and xenon; oxygen; nitrogen; a halogen such as fluorine, chlorine and bromine; $CO_2$; CO; a chlorofluorocarbon (CFC), i.e., a volatile derivative of methane, ethane or propane containing carbon, chlorine and fluorine only, e.g., dichlorodifluoromethane; or a combination thereof.

In certain embodiments, generation, i.e., formation, of unstable radicals in the sample in step (ii) of the method of the invention is carried out by electrical ionization of the gas environment in the sealed vessel. In particular such embodiments, electrical ionization is carried out by sustaining an electrical current, e.g., electrical discharge, through said gas environment as the conducting material, for a sufficient period of time. More particular such embodiments are those wherein the electrical current is of up to a few milliampere (mA), more particularly from 10 microampere (µA) to 5 mA, e.g., 0.01-1 mA or 0.05-0.5 mA, depending inter alia on the sample size; and/or sustained for up to 5 minutes, e.g., for about 15-240 seconds, about 30-210 seconds, about 90-150 seconds, or about 2 minutes.

In other embodiments, generation of unstable radicals in the sample in step (ii) is carried out by subjecting the sample in the sealed vessel to ionizing radiation with an energy not less than ($\geq$) 25 eV or a frequency not less than ($\geq$) 6 penta Hz, i.e., $6\times10^6$ GHz, mechanical agitation, or heat treatment.

The term "ionizing radiation" as used herein refers to a radiation that carries enough energy (i.e., at least 5 eV) to liberate electrons from atoms or molecules, thereby ionizing them, and composed of energetic subatomic particles, ions or atoms moving at relativistic speeds, and electromagnetic waves on the high-energy end of the electromagnetic spectrum. In certain embodiments, the ionizing radiation according to the present invention is gamma radiation, also known as gamma rays, X-radiation (composed of X-rays), or the higher ultraviolet (UV) part of the electromagnetic spectrum.

The radicals generated in the sample in step (ii) of the method of the invention are fixed to the solid and are thus prevented from any possible interaction, i.e., contacting with other possible reaction partners, and consequently do not decay. An additional factor contributing to the stability of those radicals is the diluted environment inside the sealed vessel, optionally set prior to, during, or immediately after, step (ii), either by evacuating gas from the said vessel or by introducing a suitable gas into said vessel while creating a pressure that is lower than the initial pressure in the vessel. Depending on the type of the material treated, in certain embodiments, those radicals are stable for tens of minutes and up to several (e.g., 1, 2, 3, or more) days under moderate conditions, e.g., provided that the sample is maintained at room temperature (about 20° C.-25° C.).

After forming the radicals in the sample, the latter is cooled to a cryogenic temperature so as to prepare it to the DNP process. The cryogenic temperature can be any temperature in the range of 0° K to 120° K, preferably 15° K to 60° K or 15° K to 80° K, more preferably about 20° K.

The DNP process applied to the sample, after cooling to cryogenic temperature, can be any DNP process known in the art, aimed at transferring polarization from unpaired electrons to nuclei. In certain embodiments, the DNP process performed in step (iv) of the method involves microwave irradiation at a frequency of either the sum or difference of the electron and nuclear Larmor frequencies, under applied magnetic field.

As stated above, in sharp contrast to the method of WO 2014139573, which necessitates the presence of particular carbonyl groups on the material treated, the generation of radicals in the sample treated according to the method of the present invention has nothing to do with the presence of a particular group, and the material treated may thus be any material in the solid state, more particularly any organic or inorganic material containing H or OH groups or adsorbed water molecules. Indeed, in certain embodiments, the sample provided in step (i) of the method of the invention comprises a material having no carbonyl groups.

In the study described in Example 1 hereinafter, samples of a high surface area silica, an analytical-grade sucrose and an analytical-grade mannose were placed in Pyrex NMR tubes, evacuated for up to an hour by a vacuum system maintaining a moderate vacuum level of $0.5\text{-}2\times10^{-4}$ bar, and were then sealed using hot flame. Ionization of the dilute gas inside the tubes was obtained by sustaining an electrical discharge through it for about 2 minutes, and the samples prepared were then subjected to a DNP process operating at a cryogenic temperature of 20° K, with the EDIRs serving as polarizing agents. For each sample, the DNP experiment was conducted at varying microwave irradiation frequency (irradiation time of 40 sec; microwave magnetic field strength equivalent to ~800 KHz; and a repetition delay of 1 min). The EDIRs were found to have a lifetime of days under inert conditions, when kept in the sealed glass tube following preparation, but may readily annihilate and self-terminate when exposed to air, and even more so when exposed to a solvent.

Example 2 shows the preparation of a highly polarized nuclear spins containing glucose sample, carried out by a process similar to that described in Example 1, wherein activation of the sample with electricity was carried out right before inserting the sample to the magnet, which was about 48 hours after preparation (including evacuation and sealing).

The results shown in Examples 1-2 suggest that the method utilized can be used for many other materials such as those including cleavable Si—H, Si—OH, C—H, or C—OH bonds. These results show that the EDIRs generated are very effective polarizing agents, and on the other hand, possess an instability that promotes them to self-terminate upon dissolution, thereby neutralizing their toxicity and their action as relaxation agents and possibly allowing their use in an injectable MRI contrast formulation. Another possible field of applications for these EDIRs is solid-state NMR structural measurements of pharmaceutical products, which has the ability to differentiate pharmaceutical polymorphs, but is straggling with sensitivity when examining natural abundance products (i.e., products with natural isotopic composition—not enriched with NMR responsive isotopes).

In the study described in Example 3, the concentrations of radicals formed in two similar sucrose samples treated similarly in two different NMR tubes, more specifically a regular NMR tube and an NMR tube having a bulge with a diameter of about 4 cm, were compared, and as found, the bulge and the increased gas volume in the bulged tube increased the radical concentration by ~3.6 fold.

In particular embodiments, the method of the present invention is a method as defined in any one of the embodiments above, wherein the step of setting a controlled pressure and composition gas environment in said vessel is carried out prior to step (ii) by evacuating gas from the sealed vessel, e.g., by a vacuum system, maintaining a moderate vacuum level of, e.g., $0.5\text{-}2\times10^{-4}$ bar; said unstable radicals are generated by sustaining an electrical current, e.g., discharge, through said gas environment for 1-3 minutes, preferably for about 2 minutes; and said cryogenic temperature is about 20° K.

In certain embodiments, the highly polarized nuclear spins containing sample obtained by the method of the present invention is subjected to an NMR measurement. In such embodiments, the method of the invention further comprises the step of subjecting the sample obtained in step (iv) to an NMR measurement, e.g., a solid state NMR, magic-angle spinning (MAS)-NMR, a liquid state NMR measurement, or an NMR measurement for the investigation of a surface.

In other embodiments, the highly polarized nuclear spins containing sample obtained by the method of the present invention is administered to a subject, more particularly a mammal such as an individual, undergoing a MRI scan, e.g., a metabolic MRI or functional MRI scan. In such embodiments, the sample provided in step (i) is a MRI contrast agent or a compound participating in a metabolic pathway occurring in the body of said subject, and the method of the invention further comprises the step of thawing the sample obtained in step (iv) and immediately administering said sample, in liquid or gaseous form, to said subject. Administration in liquid form can be carried out using any suitable parenteral mode of administration, preferably intravenously or by injection; and administration in gaseous form can be carried out, e.g., by inhalation of the gaseous material.

The term "metabolic pathway" as used herein refers to both anabolic pathway, i.e., a metabolic pathway that requires energy and synthesizes molecules (e.g., the synthesis of sugar from $CO_2$, the synthesis of large proteins from amino acid building blocks, and the synthesis of new DNA strands from nucleic acid building blocks), as well as to catabolic pathway, i.e., a metabolic pathway that produces energy and breaks down molecules (e.g., breaking down complex molecules into simpler ones such as where glucose is broken down, i.e., oxidized, to $CO_2$ and water).

In another aspect, the present invention provides a sample comprising highly polarized nuclear spins obtained by the method of the invention consisting of steps (i) to (iv) as defined in any one of the embodiments above.

A dissolution DNP system for carrying out the method of the present invention can be divided into two subsystems, wherein the first subsystem is a radical generator utilized for the generation of unstable radicals in the sample treated according to step (ii) of the method, and the second subsystem is a dissolution DNP polarizer, which may consist of any commercially available components modified if and as necessary.

A particular radical generator described herein can be used in a dissolution DNP system based on EDIRs according to the method disclosed and exemplified herein. In a particular embodiment schematically illustrated in FIGS. 8-9, such a radical generator 100 comprises: (i) a sample tube 200 having (a) at least one opening 204 comprising a valve, for optionally introducing a powdery sample 203 and/or a solvent therein, and for evacuating gas from said sample tube and/or introducing a desired gas or gas composition therein; (b) optionally an additional opening capable of being hermetically sealed for inserting a powdery sample; and (c) optionally two internal electric contacts 104 for connecting to an external electric power source 102 and carrying electric power to cause electrical breaching of the atmosphere within said sample tube; (ii) optionally an inductor 105 surrounding said sample tube 200, for connecting to a high frequency alternating current (AC) electric power source and carrying electric power to induce a strong circular electric field within said sample tube 200 to thereby sustain an electric arc within said sample tube; (iii) an atmosphere control unit 103 for connecting to said at least one opening 204, for evacuating gas from said sample tube 200 and/or introducing a desired gas or gas composition into said sample tube 200; and (iv) optionally an electric power source 102 for connecting and providing electric power to either said two internal electric contacts 104 or said inductor 105, provided that either said two internal electric contacts 104 or said inductor 105 is present.

Figure 8:
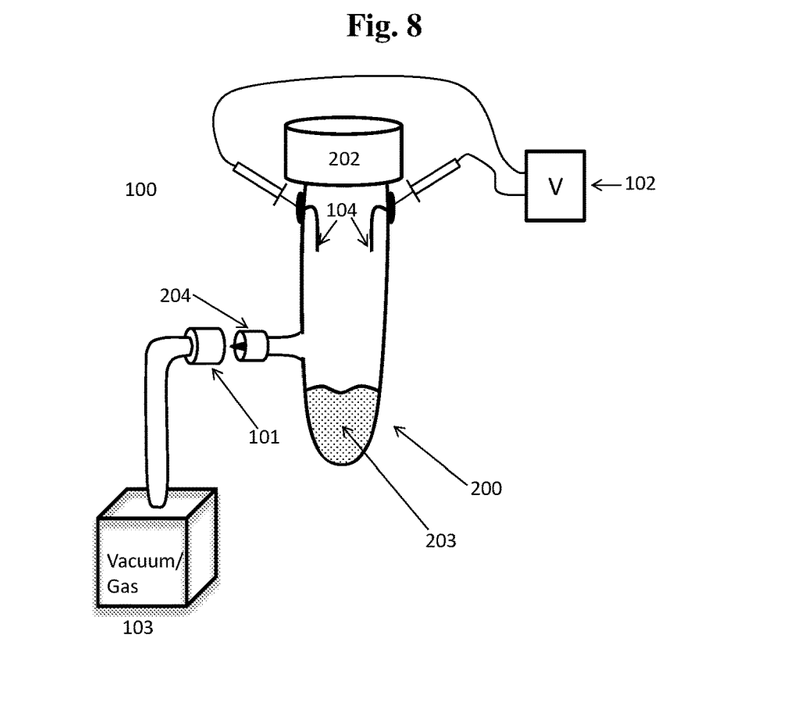
FIG. 8 illustrates one particular configuration of a radical generator for generating unstable radicals in a sample treated according to step (ii) of the method of the present invention.
Figure 9:
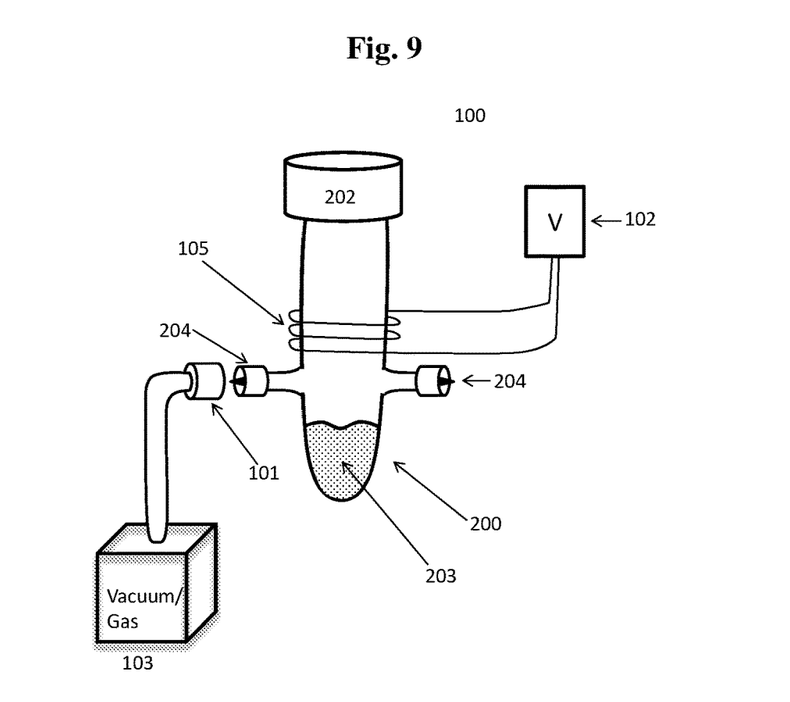
FIG. 9 illustrates another particular configuration of a radical generator for generating unstable radicals in a sample treated according to step (ii) of the method of the present invention.

In certain embodiments, the radical generator 100 of the invention comprises an inductor 105 surrounding said sample tube 200, and said optional two internal electric contacts 104 are absent.

In other embodiments, the sample tube 200 comprises two internal electric contacts 104 for connecting to an external electric power source 102, and said inductor 105 is absent.

In certain embodiments, the sample tube 200 comprises an additional opening for inserting a powdery sample, which is hermetically sealed using a cork 202.

In certain embodiments, the sample tube 200 comprises a single opening 204 (FIG. 8) comprising a two-way valve and serving as an inlet and outlet for both evacuating gas from said tube and for introducing, i.e., refilling, a desired gas or gas composition into said tube, or vise-versa. In other embodiments, the sample tube 200 comprises two openings 204 (FIG. 9), each comprising either one-way or two-way valve. It should be noted that the number of openings 204 in said sample tube 200 is independent of the overall structure of the sample tube and said radical generator 100, i.e., the sample tube 200 may comprise either a sole or two or more openings 204, no matter whether said tube comprises two internal electric contacts 104 or said radical generator comprises an inductor 105.

In certain embodiments, one or two of said openings 204 further serve as an inlet and/or outlet of a solvent. Alternatively, the sample tube 200 further comprises at least one additional opening comprising a valve, which serves as an inlet and/or outlet of a solvent, e.g., an organic solvent or an inorganic solvent, more particularly water. In a specific such embodiment, one of said at least one additional opening is located at the bottom of said sample tube 200 for evacuation of the solvent. In yet another specific embodiment, said solvent may be introduced into said sample tube 200 via its additional opening, when present, by simply removing the cork 202 therefrom. In such a case, said solvent may also be extracted from said sample tube 200 via said additional opening.

In certain embodiments, said two internal electric contacts 104 are associated with said electric power source 102 by direct contact, e.g., via a filament traversing said sample tube's wall.

In certain embodiments, said atmosphere control unit 103 is designed to control the inner pressure and gas composition within said sample tube 200. In a more specific embodiment, said unit 103 comprises at least one sensor, such as a pressure sensor, a gas sensor (e.g., oxygen sensor) and/or a gas-flow sensor, for measuring the inner pressure and/or gas composition within said sample tube 200. Said atmosphere control unit 103 may further comprise or be associated-with a vacuum or pressure generating unit, such as a pump, for generating a reduced pressure within said sample tube 200 and/or for pumping gas or gas-composition into said sample tube 200. In a more specific embodiment, said atmosphere control unit 103 further comprises or is associated with a gas container for holding the gas or gas-composition designated for insertion into said sample tube 200.

According to one possible specific mode of operation of the radical generator 100 of the invention, a sample 203 is inserted into the sample tube 200, which is then sealed, e.g., with a cork 202. The tube 200 is then connected to the atmosphere control unit 103, e.g., via a designated connector to at least one of the opening(s) 204 of the sample tube 200. The atmosphere control unit 103 then sets the conditions inside the sample tube 200 by evacuating gas therefrom or introducing a suitable gas into said tube and creating a pressure lower than the initial pressure in said tube. Next, the electric source 102 transmits power to the sample tube 200, either through said internal electric contacts 104 via said filaments or through said external inductor coil 105, to cause electrical breaching of the atmosphere within the sample tube 200 and consequently induce and sustain an electric arc within the sample tube for a desired duration. The activated sample obtained following this process may then be transported to a dissolution DNP polarizer for further use.

A dissolution DNP polarizer is based on a standard design which consists of the following main components: a magnet, a resonant cavity suitable for the desired frequencies, a MW source suitable for the desired frequencies and power requirements, a refrigeration system for the Kelvin range, a high throughput flushing system to quickly flush out polarized sample and inject into a subject or patient. The sample tube 200 with the activated sample (having the plasma-generated radicals in it) can be placed in the DNP polarizer, as any other radical contacting sample, and be subjected to the DNP polarizing process and dissolution of cooling, MW irradiation, and the subsequent flushing with hot water through the two vales in the sample tube or through the cork.

The present radical generator 100 of the invention may stand alone or be incorporated within a dissolution DNP polarizer to form a single machine.

Unless otherwise indicated, all numbers expressing, e.g., time periods or temperatures, as used in this specification, are to be understood as being modified in all instances by the term "about". Accordingly, unless indicated to the contrary, the numerical parameters set forth in this specification and attached claims are approximations that may vary by up to plus or minus 10% depending upon the desired properties to be obtained by the present invention.

The invention will now be illustrated by the following non-limiting Examples.

EXAMPLES

Example 1. Preparing Highly Polarized Nuclear Spins Containing Samples of Silica, Sucrose and Mannose Three types of samples were tested in our DNP experiments. The first is a high surface area silica, used for liquid chromatography (LiChrosorb® Si 60 by Merck); the second is an analytical-grade sucrose (from JT Baker); and the third is an analytical-grade mannose (from Sigma). The LiChrosorb® Si 60 product was used as is, while the latter two materials were manually pulverized to a fine powder using a pestle and a mortar. The materials were placed in Pyrex NMR tubes (Wilmad), evacuated for up to one hour by a vacuum system maintaining a moderate vacuum level of $0.5-2\times10^{-4}$ bar, and then sealed using a hot flame. Ionization of the dilute gas inside the tubes was obtained by sustaining an electrical discharge through it for about 2 minutes using a commercial spark discharge tool (Electro-Technic Products model BD-10A). This action created free radicals on the solid sample that persisted over a few days (based on their ESR signal) as long as the sample tubes remained sealed.

Figure 1A:
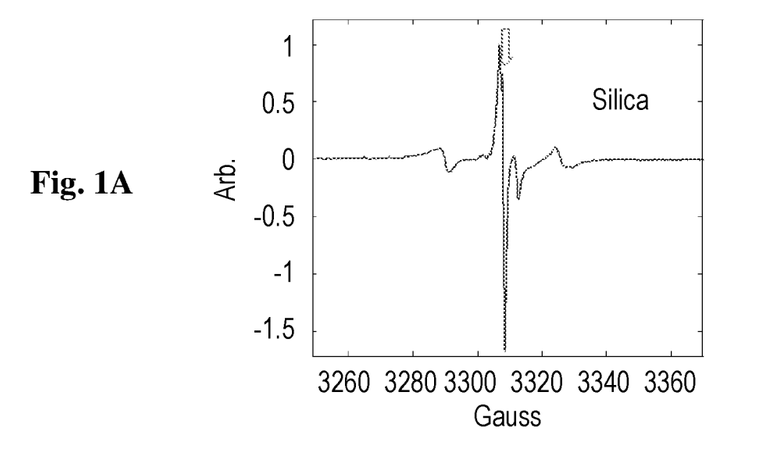
FIGS. 1A-1C show ESR signal of EDIRs, as measured at room temperature by a Bruker CW system (EMX), at a frequency of 9.21 GHz, for silica (1A), sucrose (1B) and mannose (1C). The arrows show the position of the signal from a reference trityl sample used for quantifying spin concentration and g factor.
Figure 1B:
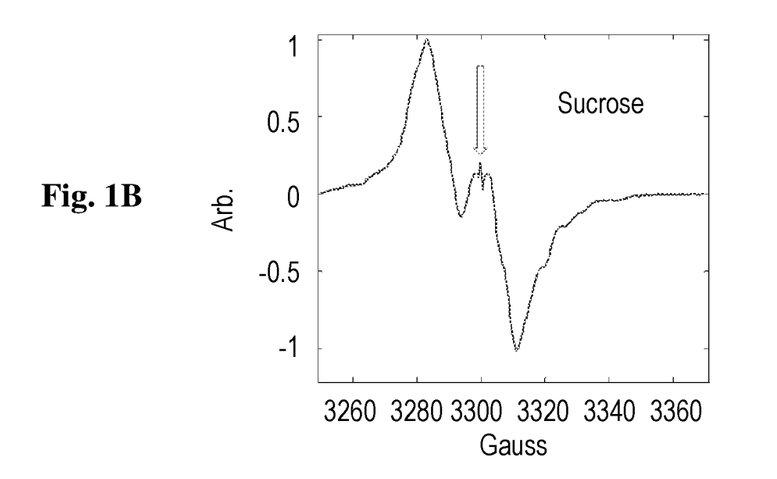
Figure 1C:
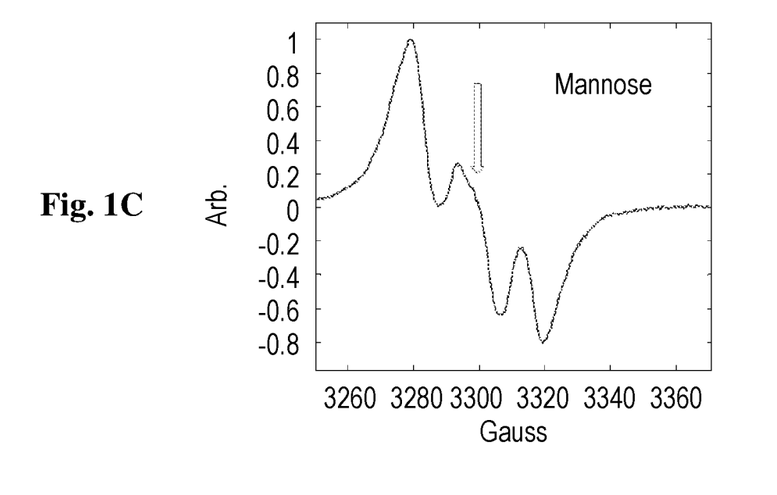
Figure 2A:
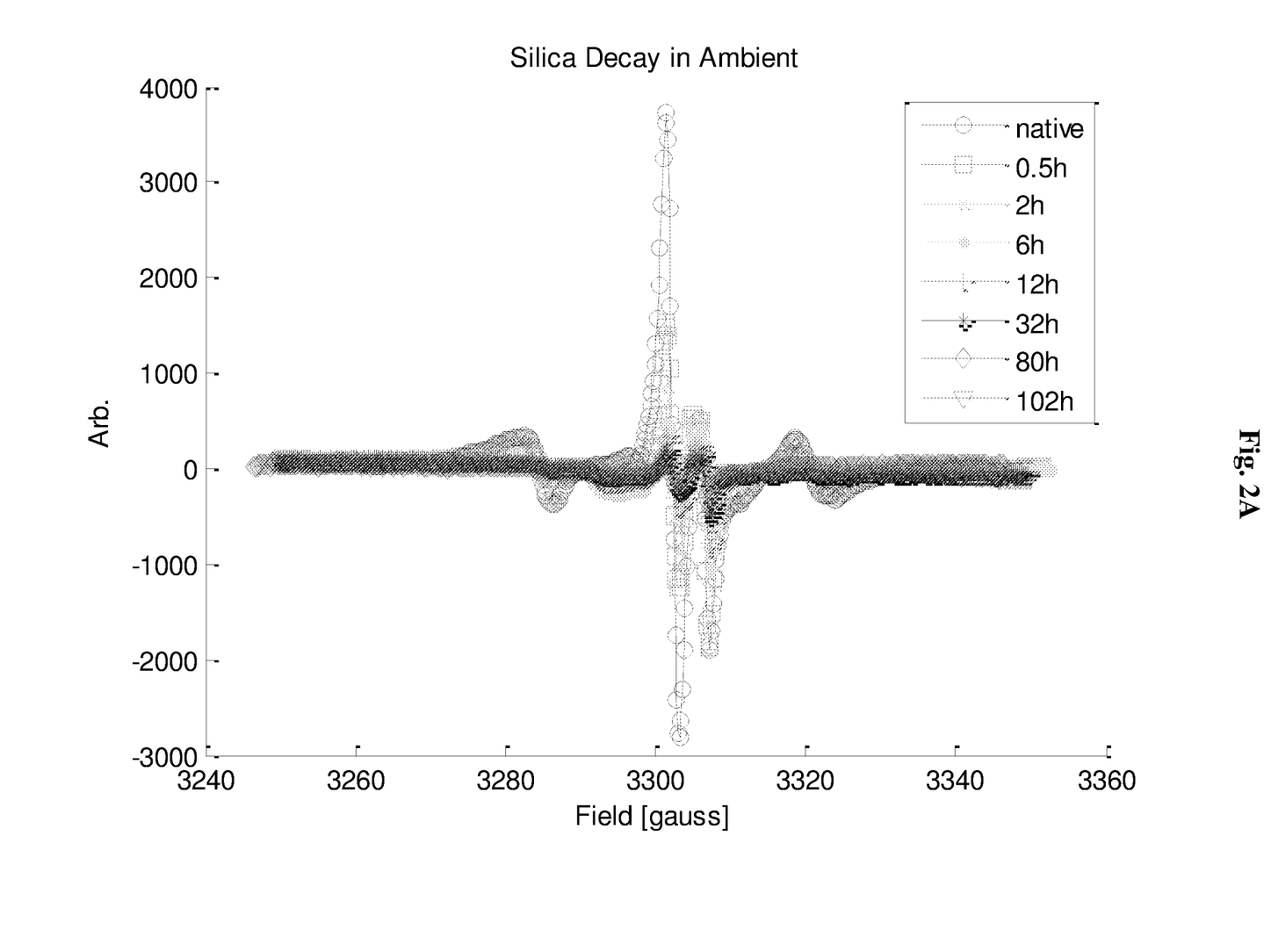
FIGS. 2A-2D show ESR signal of EDIRs in silica (2A-2B) and sucrose (2C-2D), as a function of time. Baseline plot represents the signal of the sealed tubes after preparation, while the other plots show the signal as a function of time after opening the air seal of the tubes.
Figure 2B:
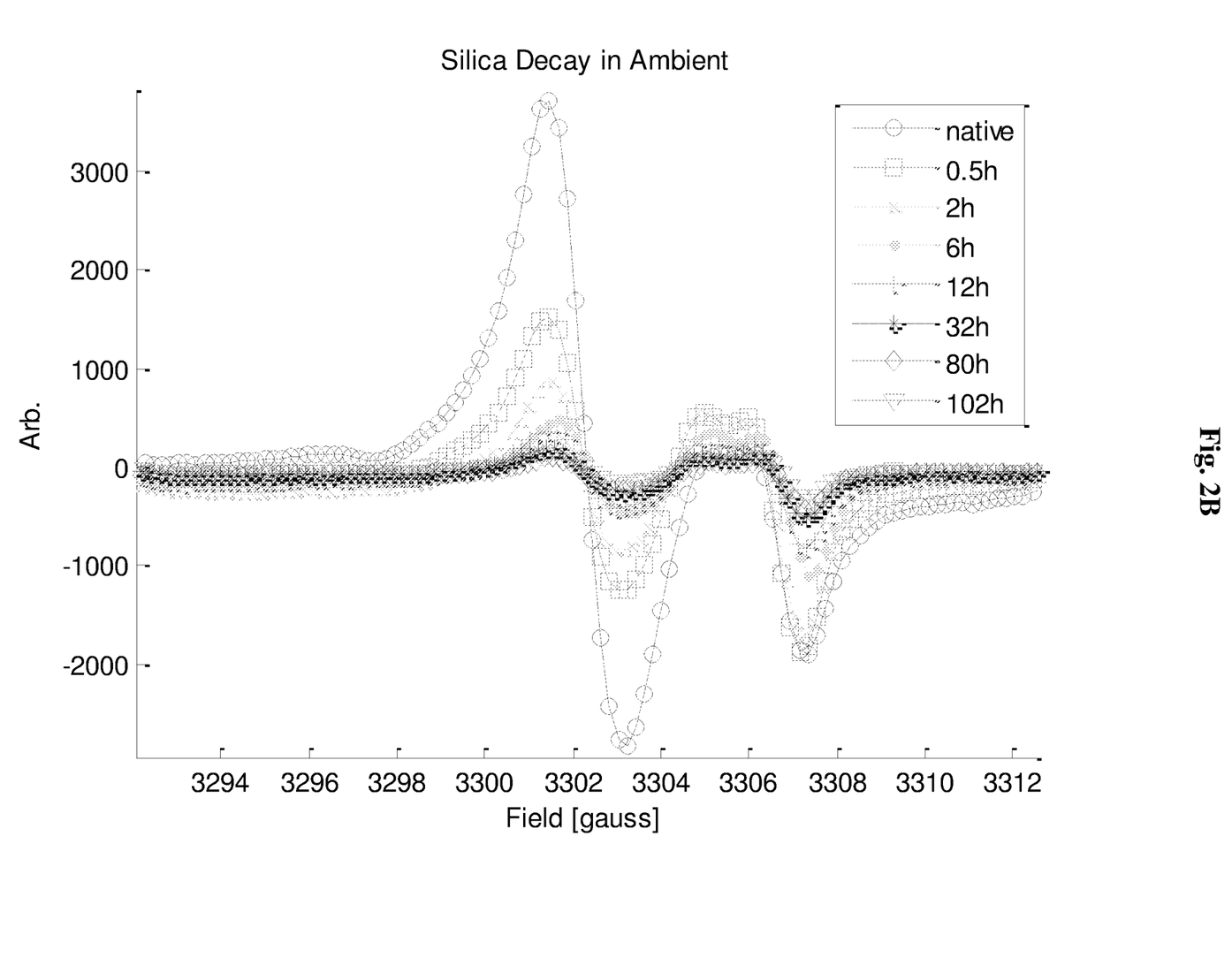
Figure 2C:
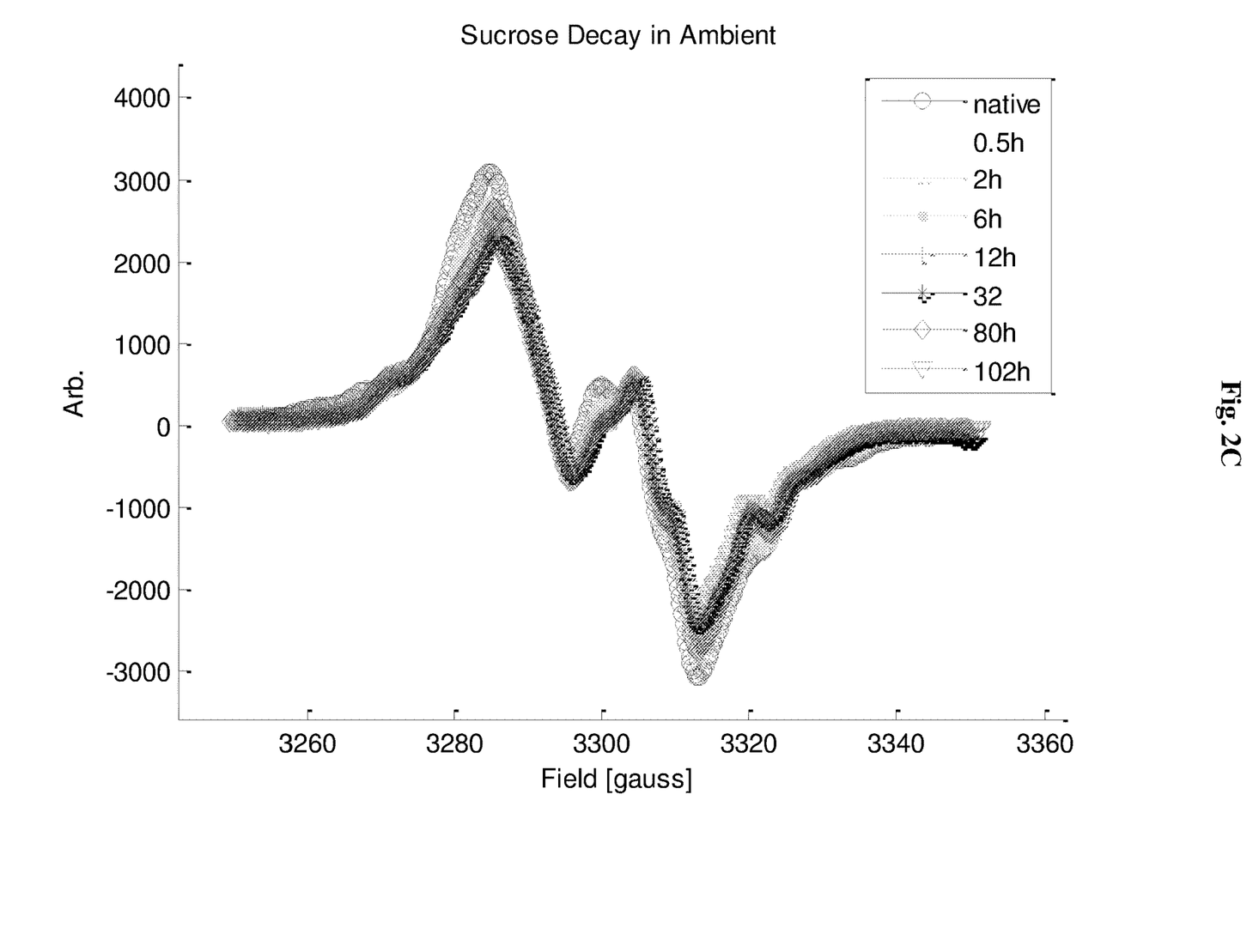
Figure 2D:
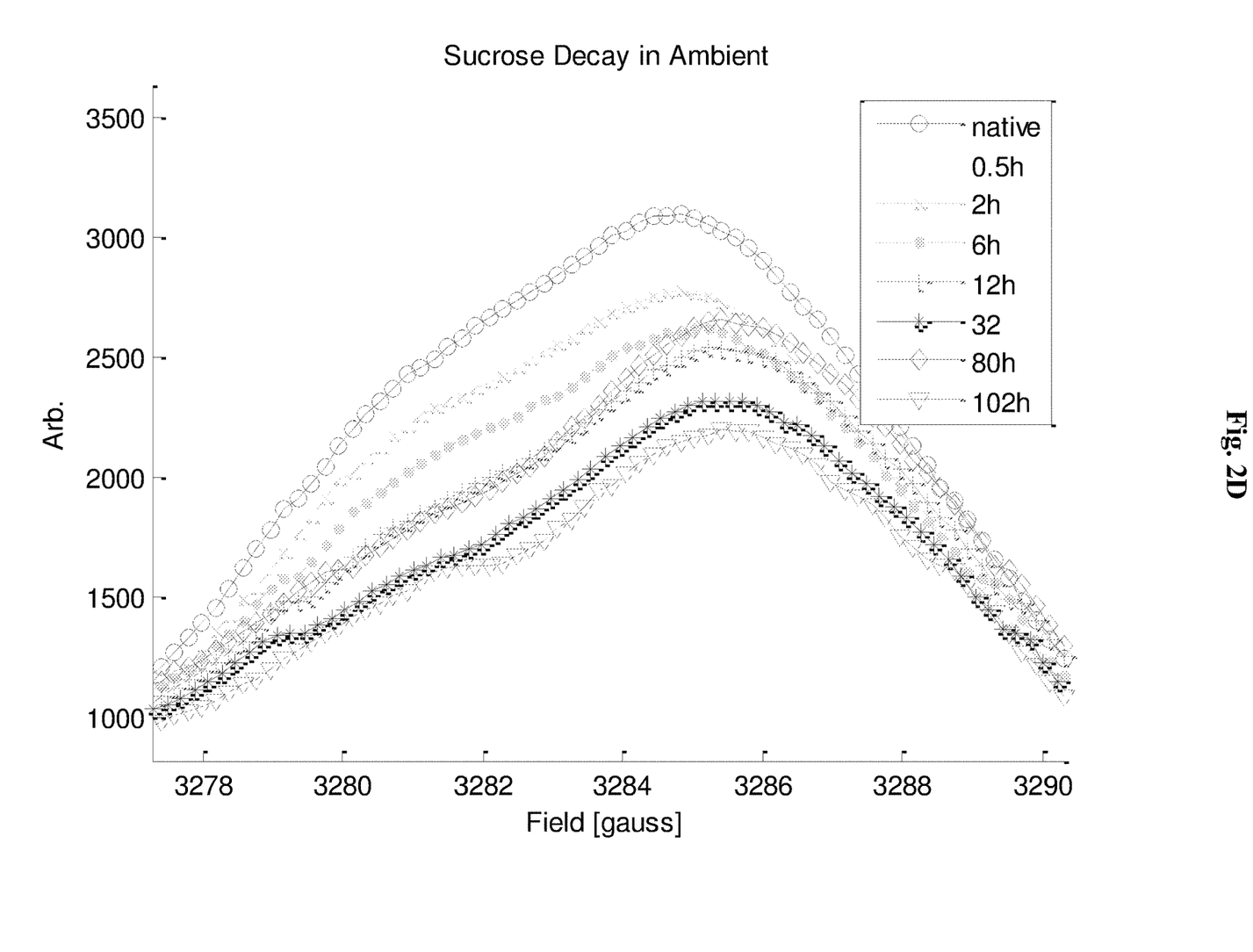

FIG. 1 shows the ESR spectra of the three samples immediately after preparation. The spin concentration was estimated using a 10-μM trityl free radical reference sample and was found to be around $1.7\times10^{14}$, $2.4\times10^{15}$ and $4.6\times10^{14}$ spins per mg for the silica, sucrose and mannose samples, respectively. These EDIRs can be assigned based on their spectra and the chemical properties of the samples' surfaces. For example, the radicals in the silica sample are most likely the result of $Si^-$ and $SiO_-$ broken bonds on the surface of the silica, which is known to be capped by O and OH groups or by a combination of $H_2O$ and OH groups (Zhuravlev, 2000; Radzig, 2000; Giordano et al., 2007). The EDIRs in the irradiated sucrose powder have the same characteristics as those measured by γ-irradiation of sucrose single crystals, which have been identified as carbon-centered radicals based on hydrogen-extracted species (Ueda et al., 1961). Similar spectra and analysis of radical structures were obtained for the case of argon plasmolysis of amylase (Kuzuya et al., 1994). The radicals formed in the mannose sample following the electrical discharge preparation also resemble very much those generated by γ-irradiation, which were assigned through DFT calculations to a C-3 centered radical (Guzik et al., 2012). It can be concluded that all radicals generated in our experiments are likely to be formed by cleavage of H atoms and/or OH groups by the ionized plasma gas.

Further evidence to the nature of the EDIRs can be found by monitoring their ESR signal over time, following the exposure of the sample tube to the atmosphere. FIG. 2 shows the resulting signal decay. For silica (FIG. 2A-2B) the signal decays fast upon air exposure and continues to decay at a slower rate over time and until it is practically gone after ~3 days. For sucrose (FIG. 2C-2D) there is also a fast initial decay, but after that there is not much change. These findings imply that in silica practically all the radicals are on the surface and accessible to air, while in sucrose, just ~20-30% of the radicals are air accessible.

DNP experiments were conducted on a homemade instrument (Feintuch et al., 2011) employing a 3.4-tesla superconducting magnet equipped with a dual NMR-ESR probe head for simultaneous excitation of both electron and nuclear spins, operating at a cryogenic temperature of 20 K. The DNP experiment was conducted at varying microwave (MW) irradiation frequencies for each sample. At every MW frequency, these experiments used MW irradiation time of 40 sec with MW magnetic field ($B_1$) strength equivalent to ~800 KHz, and a repetition delay of 1 min before the next MW frequency was tested. The results of these measurements are shown in FIG. 3.

Figure 3A:
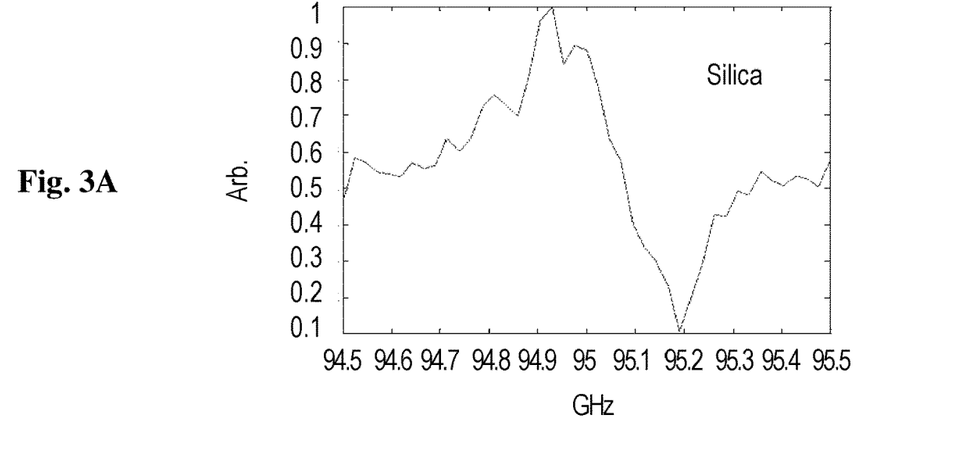
FIGS. 3A-3C show DNP NMR signal enhancement plots for silica (3A), sucrose (3B) and mannose (3C) as a function of microwave frequency. When the microwave frequency is distant from the radicals-nuclei forbidden transition frequency (see FIG. 1), the NMR signal should reflect normal thermal polarization signal. When the microwave frequency is close to the radicals-nuclei forbidden transition frequency, the nuclear polarization can be enhanced either to the positive or to the negative side.
Figure 3B:
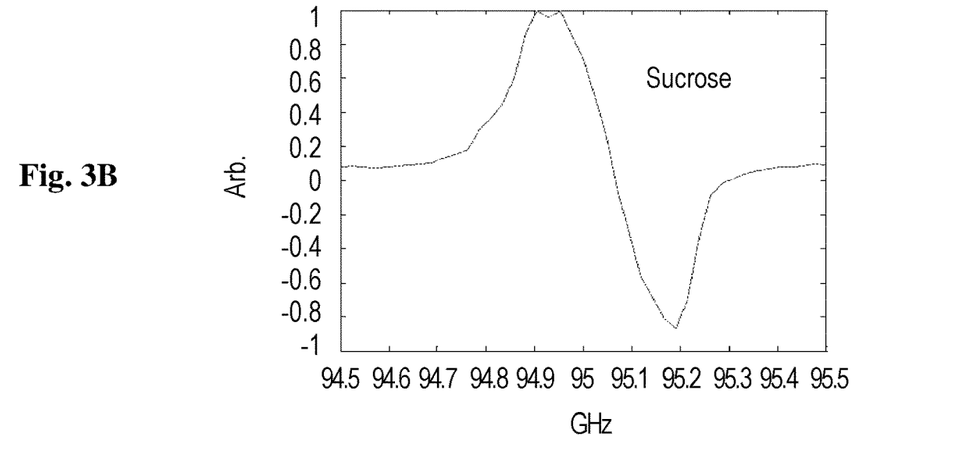
Figure 3C:
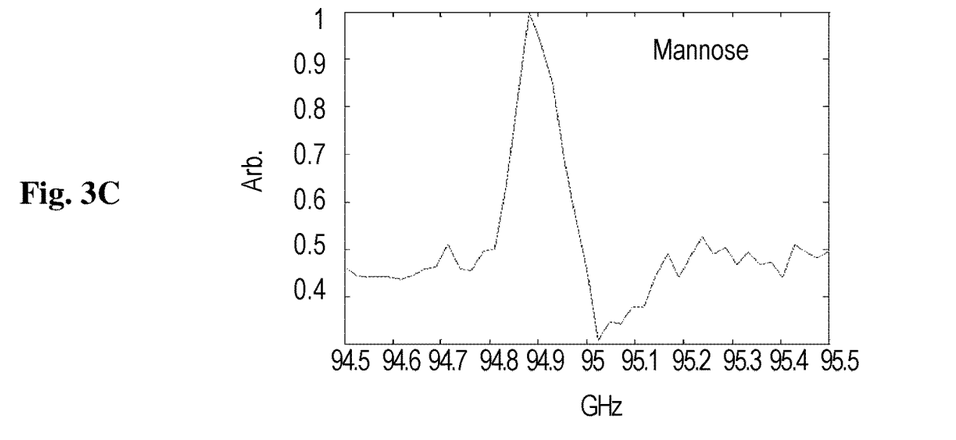

FIG. 3 demonstrates the DNP enhancement of the magnetization, with the EDIRs serving as polarizing agents. Enhancement factors of E≈1-2 for silica and mannose, and E≈17 for sucrose, are apparent. These radicals may herald a new class of polarizing agents with various desirable characteristics.

Figure 4:
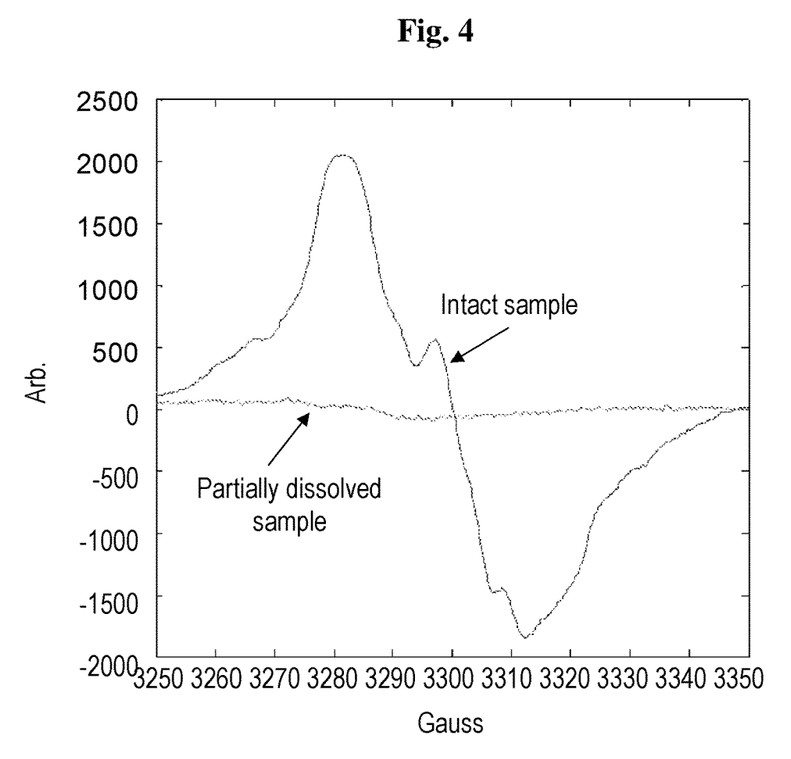
FIG. 4 shows ESR signal from sucrose sample before and after exposure to a solvent.

When not exposed to air (i.e., kept at room temperature in the sealed glass tube following preparation), the EDIRs were found to have a lifetime of days (data not shown). On the other hand, as noted above, they readily annihilate and self-terminate when exposed to air, and especially to a solvent. A typical experiment of this sort is presented in FIG. 4. The signal from the EDIRs imparted on a sucrose sample was first measured by CW ESR system immediately after preparation. Subsequently, we introduced a solvent (50/50 water ethanol) to the sample and repeated the measurement. The results show that only a small residual signal remains, indicating a high yield destruction of EDIRs. We note that the introduction of the solvent and subsequent measurements were done as quickly as possible (~few seconds), in order to simulate the short time available for neutralization of free radicals in an actual medical dissolution DNP experiment. The short time frame and the use of a rather primitive experimental setup did not allow for complete dissolution of the sucrose, hence, it is possible that the residual signal stems from the small portion of the sample that failed to dissolve.

As shown by our results, the applicability of our technique to various distinct samples of quite different character is suggestive of good prospective applications to other materials as well, many of which include cleavable Si—H, Si—OH, C—H, or C—OH bonds. It is expected that such cleavable bonds readily return to their native diamagnetic state upon introduction of water as solvent or water vapor in air. This turns EDIRs into very attractive polarizing agents to be used in the technique of dissolution DNP for clinical applications. On the one hand, they are good polarizing agents; and on the other hand, they possess an instability that makes them self-terminate upon dissolution, thereby neutralizing their toxicity and possibly allowing their use in an injectable MRI contrast formulation. Another possible field of application for these EDIRs is for solid-state NMR structural measurements of pharmaceutical products, which has the ability to differentiate pharmaceutical polymorphs, but struggle with sensitivity when examining natural abundance products (Holzgrabe et al., 1998). Here, the examinations must be made on the native solid substance and no solution can be added, which is problematic for the currently existing solid state DNP approached.

Example 2. Preparing Highly Polarized Nuclear Spins Containing Sample of Glucose In this experiment, we carried out measurements on a sample of glucose which contained 27.1 mg after filling and 25.8 mg after sealing, at a pressure of $0.12 \times 10^{-4}$ bar. The activation of the sample with electricity was carried out right before inserting the sample to the magnet, which was about 48 hours after preparation (including evacuation and sealing).

Figure 5:
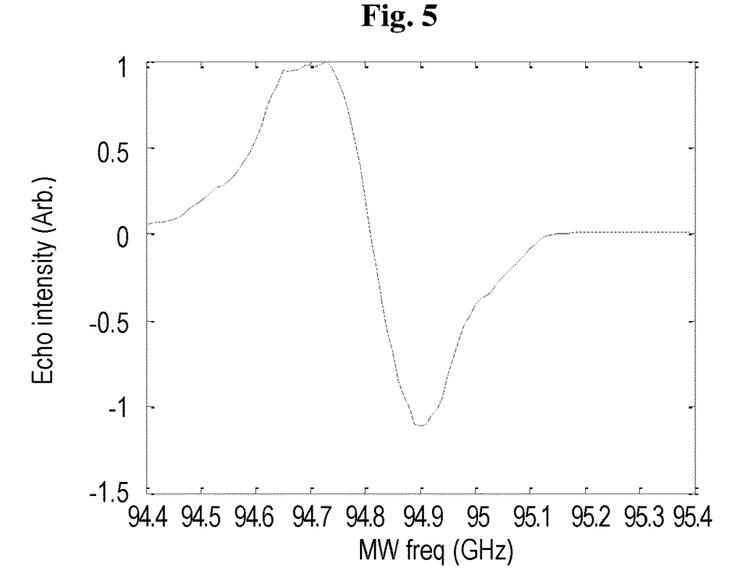
FIG. 5 shows DNP NMR signal enhancement plot for glucose, as a function of the microwave frequency.

DNP experiments were conducted as described in Example 1. In particular, we scanned the echo intensity as a function of microwave (MW) frequency, while varying it from 94.4 GHz to 95.4 GHz in 100 steps of 10 MHz. The DNP of glucose as a function of the MW frequency is shown in FIG. 5, indicating that the maximal polarization transfer was achieved at 94.67 GHz, where an increase of a factor of 20 in the NMR signal is shown.

Figure 6:
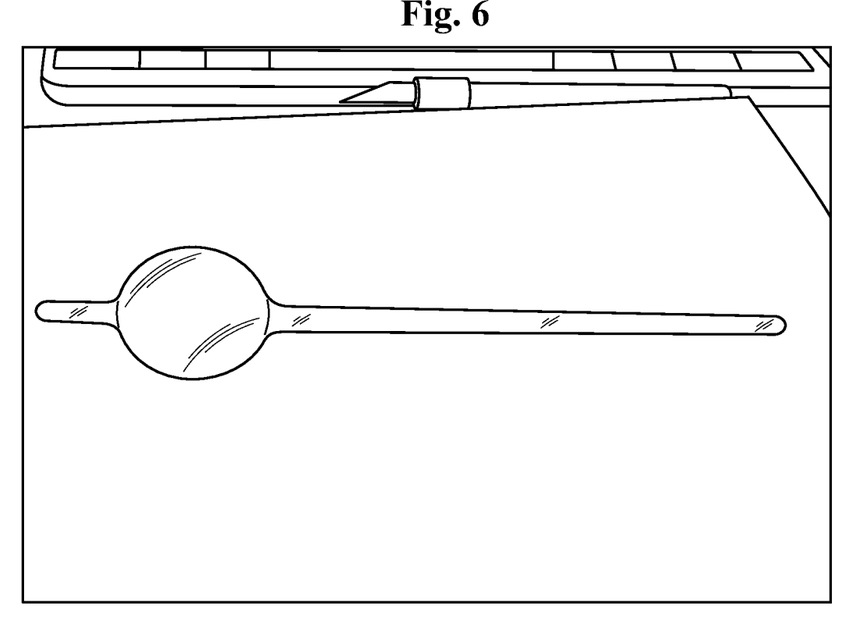
FIG. 6 shows an NMR tube having a spherical bulge with a diameter of about 4 cm, as used in the experiment described in Example 3.

Example 3. Enhancing Radical Concentration in Electrical Discharge Activated Samples In this experiment, the concentrations of radicals formed in two similar sucrose samples treated in two different NMR tubes were compared. Each one of the sucrose samples was crushed with pastel and mortar, and then placed in an NMR tube, evacuated and sealed; however, while one of the tubes was ordinary, the other tube had a spherical bulge in it with a diameter of about 4 cm, as show in FIG. 6. The amount of sucrose provided in each one of the tubes was similar, wherein the regular tube contained 12.8 mg of crushed glucose and the tube with the bulge contained 13 mg of the same substance. Both tubes were evacuated to roughly the same pressure (about 0.1 mbar), and both were electrocuted before measurement with vigorous ark roughly the same manner.

Figure 7:
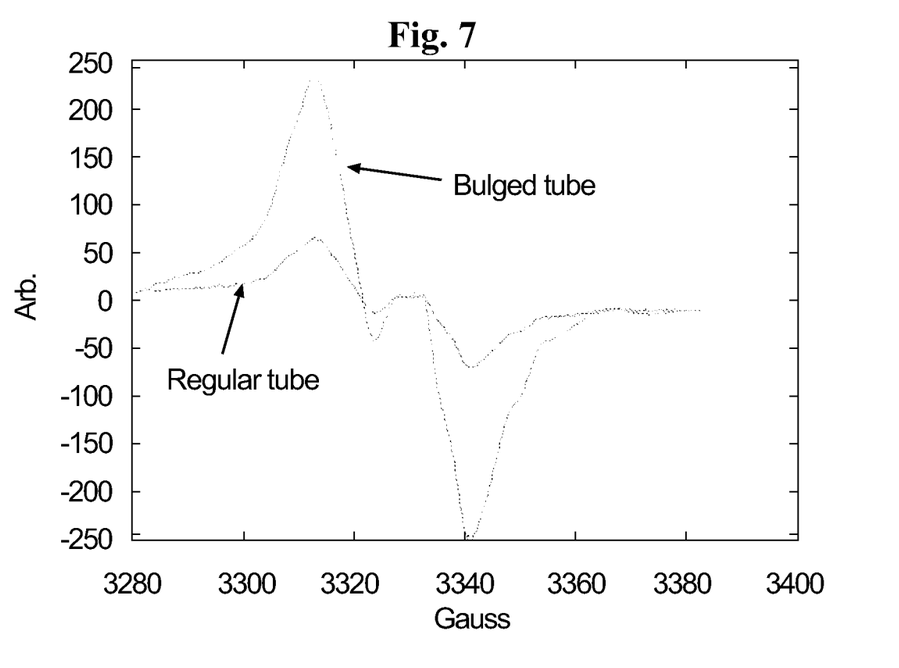
FIG. 7 shows ESR signals of EDIRs, measured at room temperature, for two sucrose samples treated roughly the same manner in two different NMR tubes, as described in Example 3.

The ESR measurement was done with one 163 sec long scan, over a 3280-3380 gauss range (modulation frequency of 100 KHz; amplitude of 1 gauss; regular attenuation of 25 db; and 512 ample points). The samples were measured quickly one after the other in more or less the same conditions, and the results are shown in FIG. 7, indicating that the bulge and the increased gas (plain air) volume in the bulged tube increases the radical concentration by ~3.6 fold.

REFERENCES

Abragam A., Goldman M., *Rep. Prog. Phys.*, 1978, 41, 395
Ardenkjaer-Larsen J. H., Fridlund B., Gram A., Hansson G., Hansson L., Lerche M. H., Servin R., Thaning M., Golman K, *Proc. Nat. Acc. Sci.*, 2003, 100-18, 10158
Ardenkjaer-Larsen J. H., Leach A. M., Clarke N., Urbahn J., Anderson D., Timothy W. Skloss T. W., *NMR Biomed.*, 2011, 24, 927
Barnes A. B., De Paëpe G., Van Der Wel P. C. A., Hu K. N., Joo C. G., Bajaj V. S., Mak-Jurkauskas M. L., Sirigiri J. R., Herzfeld J., Temkin R. J., Griffin R. G., *App. Mag. Res.*, 2008, 34, 237
Carver T. R., Slichter C. P., *Phys. Rev.*, 1956, 102-4, 975
Dollmann B. C., Junk M. J. N., Drechsler M., Spiess H. W., Hinderberger D., Munnemann K., *Phys. Chem. Chem. Phys.*, 2010, 12, 5879
Eichhorn T. R., Takado Y., Salameh N., Capozzi A., Cheng T., Hyacinthe J. N., Mishkovsky M., Roussel C., Comment A., *Proc. Nat. Acc. Sci.*, 2013, 110-45, 18064
Feintuch A., Shimon D., Hovav Y., Banerjee D., Kaminker I., Lipkin Y., Zibzener K., Epel B., Vega S., Goldfarb D., *J. Mag. Res.*, 2011, 209, 136
Giordano L., Sushko P. V., Pacchioni G., Shluger A. L., *Phys. Rev B*, 2007, 75, 024109
Golman K., Zandt R. I. Thaning M., *Proc. Nat. Acc. Sci.*, 2006, 103-30, 11270
Guzik G. P., Stachowicz W., Michalik J., *Nukleonika*, 2012, 57(4), 545
Holzgrabe U., Diehl B. W., Wawer I., *J. Pharm. Biomed. Anal.*, 1998, 17, 557
Hu K. N., Debelouchina G. T., Smith A. A., Griffin R. G., *J. Chem. Phys.*, 2011, 134, 125105
Kuzuya M., Noda N., Kondo S., Washino K., Noguchi A., *J. Am. Chem. Soc.*, 1992, 114(16), 6505-6512
Kuzuya M., Morisaki K., Niwa J., Yamauchi Y., Xu K., *J. Phys. Chem.*, 1994, 98, 11301
Lesage A., Lelli M., Gajan D., Caporini M. A., Vitzthum V., Mieville P., Alauzun J., Roussey A., Thieuleux C., Mehdi A., Bodenhausen G., Coperet C., Emsley L., *J. Am. Chem. Soc.*, 2010, 132, 15459
Maly T., Debelouchina G. T., Bajaj V. S., Hu K. N., Joo C. G., Mak-Jurkauskas M. L., Sirigiri J. R., Van Der Wel P. C. A., Herzfeld J., Temkin R. J., Griffin R. G., *J. Chem. Phys.*, 2008, 128, 052211
Mishkovsky M., Comment A., Gruetter R., *J. Cer. Blood Flow & Met.*, 2012, 32, 2108
Nelson S. J., Kurhanewicz J., Vigneron D. B., Larson P. E. Z., Harzstark A. L., Ferrone M., van Criekinge M., Chang J. W., Bok R., Park I., Reed G., Carvajal L., Small E. J., Munster P., Weinberg V. K., Ardenkjaer-Larsen J. H., Chen A. P., Hurd R. E., Odegardstuen L. I., Robb F. J., Tropp J., Murray J. A., *Sci. Trans. Med.*, 2013, 5(198), ra108
Pinon A. C., Rossini A. J., Widdifield C. M., Gajan D., Emsley L., *Mol. Pharm.*, 2015, 12, 4146-4153
Radzig V. A., in Pacchioni G., Skuja L., Griscom D. L., Eds., Defects in $SiO_2$ and related dielectrics: Science and Technology, Kluwer Academic Publishers: Dordrecht, The Netherlands, 2000, 2, 339
Rossini A. J., Widdifield C. M., Zagdoun A., Lelli M., Schwarzwälder M., Copéret C., Lesage A., Emsley L., *J. Am. Chem. Soc.*, 2014, 136, 2324-2334
Song C., Hu K. N., Joo C. G., Swager T. M., Griffin R. G., *J. Am. Chem. Soc.*, 2006, 128, 11385
Ueda H., Kuri Z., Shida S., *J. Chem Phys.*, 1961, 35, 2145
Zhuravlev L. T., *Colloids and Surfaces A: Physicochem. Eng. Aspects*, 2000, 173, 1

What is claimed is:
1. A method for the preparation of a sample comprising highly polarized nuclear spins, said method comprising:
(i) providing a sample in the form of a powdery solid, in a sealed vessel;

(ii) setting a controlled pressure and composition gas environment in said vessel by evacuating gas from said vessel maintaining a moderate vacuum level of $1\times10^{-6}$ to $1\times10^{-3}$ bar, (iii) generating unstable radicals in said sample by electrical ionization of the gas environment for 1-3 minutes, wherein said unstable radicals are fixed to the solid and thus do not decay for tens of minutes and up to several days under moderate conditions;

(iv) cooling said sample to a cryogenic temperature in the range of 0° K to 120° K; and (v) performing a dynamic nuclear polarization (DNP) process on the cooled sample so as to transfer spin polarization from the electron spins to the nuclear spins, thereby obtaining said sample comprising highly polarized nuclear spins.

2. The method of claim 1, wherein the DNP process performed in step (v) involves microwave irradiation at a frequency of either the sum or difference of the electron and nuclear Larmor frequencies, under an applied magnetic field.

3. The method of claim 1, wherein the sample provided in step (i) comprises a material having no carbonyl groups.

4. The method of claim 1, further comprising the step of subjecting the sample obtained in step (v) to a nuclear magnetic resonance (NMR) measurement.

5. The method of claim 4, wherein said NMR measurement is solid state NMR, magic-angle spinning (MAS)-NMR, a liquid state NMR measurement, or an NMR measurement for the investigation of a surface.

6. The method of claim 1, further comprising the step or thawing the sample obtained in step (v) and immediately administering said sample, in liquid or gaseous form, to a subject undergoing a magnetic resonance imaging (MRI) scan.

7. The method of claim 6, wherein said MRI scan is metabolic MRI or functional MRI.

* * * * *